United States Patent
Wang et al.

(10) Patent No.: US 11,246,836 B2
(45) Date of Patent: Feb. 15, 2022

(54) INTRAMUSCULAR DEPOT OF DECOQUINATE COMPOSITIONS AND METHOD OF PROPHYLAXIS AND TREATMENT THEREOF

(71) Applicant: BLUELIGHT PHARMATECH CO., LTD., Guangdong (CN)

(72) Inventors: Hongxing Wang, Guangdong (CN); Shuanghong Liang, Guangdong (CN); Yinzhou Fan, Guangdong (CN); Xiaoyi Huang, Guangdong (CN); Li Qin, Guangdong (CN); Xiaoping Chen, Guangdong (CN)

(73) Assignee: BLUELIGHT PHARMATECH CO., LTD., Guangdong (CN)

( * ) Notice: Subject to any disclaimer, the term of this patent is extended or adjusted under 35 U.S.C. 154(b) by 0 days.

(21) Appl. No.: 16/083,673

(22) PCT Filed: May 17, 2018

(86) PCT No.: PCT/CN2018/087307
§ 371 (c)(1),
(2) Date: Sep. 10, 2018

(87) PCT Pub. No.: WO2019/218305
PCT Pub. Date: Nov. 21, 2019

(65) Prior Publication Data
US 2021/0059946 A1    Mar. 4, 2021

(51) Int. Cl.
*A61K 9/16* (2006.01)
*A61K 9/00* (2006.01)
*A61K 31/47* (2006.01)

(52) U.S. Cl.
CPC .......... *A61K 9/1617* (2013.01); *A61K 9/0024* (2013.01); *A61K 9/1647* (2013.01); *A61K 9/1682* (2013.01); *A61K 31/47* (2013.01)

(58) Field of Classification Search
CPC ................................ A61K 47/14; A61K 47/28
See application file for complete search history.

(56) References Cited

U.S. PATENT DOCUMENTS

| | | | |
|---|---|---|---|
| 3,485,845 A | 12/1969 | Davis et al. | |
| 3,544,686 A | 12/1970 | Davis et al. | |
| 4,031,220 A | 6/1977 | Richards | |
| 4,195,089 A | 3/1980 | Richards | |
| 5,200,418 A | 4/1993 | Redman et al. | |
| 9,993,454 B2 * | 6/2018 | Singh ................... | A61K 9/1075 |
| 2009/0093427 A1 * | 4/2009 | Fisher ................ | A61K 48/0075 514/44 R |
| 2011/0287101 A1 * | 11/2011 | Guarnieri ............... | A61K 31/48 424/468 |
| 2016/0287711 A1 | 10/2016 | Salatinjants et al. | |

FOREIGN PATENT DOCUMENTS

| | | | | |
|---|---|---|---|---|
| CN | 101361711 A | | 2/2009 | |
| CN | 104906044 A | | 9/2015 | |
| WO | 0187290 A1 | | 11/2001 | |
| WO | WO-2018108163 A1 | * | 6/2018 | ............. A61P 35/00 |

OTHER PUBLICATIONS

Li, Malaria Research and Treatment, Hindawi, 2017 (Year: 2017).*
Ammar, Current Science International, 5, 3, 2016 (Year: 2016).*
Sheikh, Asian Journal of Pharmaceutics, 10, 4, 2016 (Year: 2016).*
Da Cruz, et al.: "Drug Screen Targeted at Plasmadium Liver Stages Identified a Potent Multistage Antimalarial Drug", JID 205 (2012), pp. 1278-1286.
Fry and Williams: "Effects of Decoquinate and Clopidol on Electron Transport in Mitochondria of Eimeria tenella (Apicomplexa: Coccidia)", Biochemical Pharmacology 33(2), (1984), pp. 229-240.
Li, et al.: "Long-Term Prophylaxis and Pharmacokinetic Evaluation of Intramuscular Nano- and Microparticle Decoquinate in Mice Infected with P. berghei Sporozoites", Malaria Research and Treatment (2017), Article ID 7508291, pp. 1-10.
Nam, et al.: "A Chemical Genomic Analysis of Decoquinate, a Plasmodium falciparum Cytochrome b Inhibitor", ACS Chemical Biology 6 (2011), pp. 1214-1222.
Wang, et al.: "Formulation and Particle Size Reduction Improve Bioavailability of Poorly Water-Solubel Compounds with Antimalarial Activity", Malaria Research and Treatment (2013), Article ID 769234, pp. 1-10.
Wang, et al.: "Nanoparticle formulations of decoquinate increase antimalarial efficacy against liver stage Plasmodium infections in mice", Nanomedicine: NBM 10 (2014), pp. 57-65.

* cited by examiner

*Primary Examiner* — Robert A Wax
*Assistant Examiner* — William Craigo
(74) *Attorney, Agent, or Firm* — Norton Rose Fulbright US LLP; James R. Crawford

(57) ABSTRACT

Implants comprising an antimalarial agent such as decoquinate or another therapeutic drug are disclosed. The implants can be in the form of a complex comprising a drug, a lipid or lipids and optionally a polymer carrier. The present invention provides methods for preparing implants wherein the implants comprise decoquinate or another therapeutic drug, and a lipid or lipids such as cholesterol, monoglycerides, or diglycerides, and optionally a small percentage of a biocompatible polymer based on the total implant weight. The implants are useful for releasing a therapeutic drug at a constant level and maintaining a prophylactic or therapeutic level of the drug in a subject, for preventing a malarial infection or treating other diseases or disorders.

22 Claims, 4 Drawing Sheets

Figure 1:
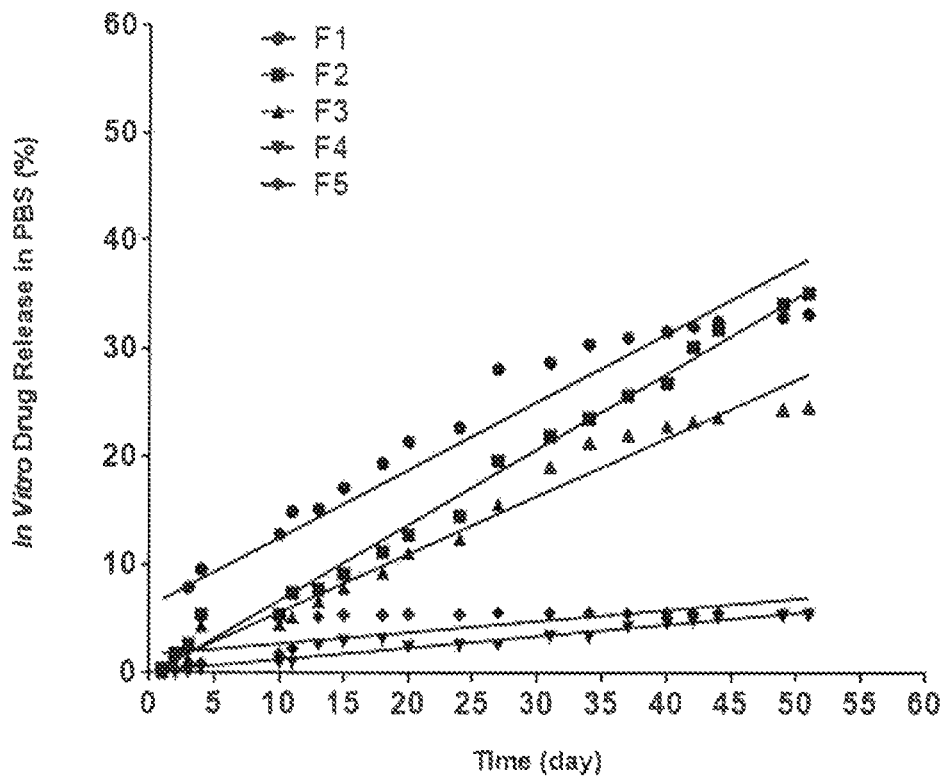

Parasitemia detection 6 days after *Plasmodium berghei* sporozoite inoculation

INTRAMUSCULAR DEPOT OF DECOQUINATE COMPOSITIONS AND METHOD OF PROPHYLAXIS AND TREATMENT THEREOF

CROSS REFERENCE TO RELATED APPLICATIONS

This application is a § 371 of International Application No. PCT/CN2018/087307 filed May 17, 2018, which is hereby incorporated by reference in its entirety.

TECHNICAL FIELD

The present invention relates to implants comprising the antimalarial (antiparasitic) agent decoquinate (also abbreviated as "DQ") or other therapeutic drugs such as other antiparasitic agents. In some embodiments, the implants are in the form of a complex comprising the drug, a lipid or lipids, and optionally a small percentage of a biocompatible polymeric carrier based on the weight of the implant. Examples of lipids include cholesterol, monoglycerides, and diglycerides. These implants provide a depot of the therapeutic drug active and are designed to release the therapeutic drug at a constant level to maintain a prophylactic or therapeutic level of the drug in a subject. The implants are useful for preventing malarial infections or treating other parasitic diseases or disorders.

BACKGROUND

Malaria is a common infectious disease that affects and threatens the lives of many people around the world. Prophylaxis of the disease through the development of vaccines against *Plasmodium* parasites has been a main effort in stopping *Plasmodium* infection before any symptoms occur. Although vaccination in preventing malaria upon mosquito bites is highly desirable, it has very limited success due to the difficulty working on readily mutated gene sequences of the parasites. An alternative prophylaxis approach for malaria is to depot a bioactive agent in the form of an implant in a subject that provides a desired level of effectiveness for a period of at least two months.

Some diseases including diabetes, hypertension, schizophrenia, rheumatoid disorders and prostate cancer require a controlled and constant release of a therapeutic agent to achieve efficacy. Noncompliance is often a concern in patients who need frequent dosing. Therefore, a method that can maintain a sufficient level of therapeutic drug for over at least one month or more without taking medication daily or more frequently would help patients comply and improve clinical outcomes. A method of delivering an agent in an implantable formulation using carrier materials that are biocompatible, and biodegradable would also reduce the discomfort for patients, particularly where conventional implants often require surgical implantation and removal of the implant.

Thus, implants for delivering prophylactic levels of decoquinate or therapeutic levels of other medications are provided in this invention.

Polymers are widely used as a formulation material for controlled release of a drug for treatment of some diseases. The polymers used for implants or controlled release formulations are typically poly D, L-lactide-co-glycolide (PLGA) with a L/G ratio of 75/25 or with a L/G ratio of 50/50. These polymers are water insoluble and when used as implant carriers must be injected with solvents selected from N-methyl-2-pyrrolidone (NMP), ethyl benzoate (EB), benzyl benzoate (BB), benzyl alcohol (BA), ethyl hydroxide (EtOH), and triacetin, or combinations thereof, among which the most commonly used non-hazardous solvent is NMP. However, in our prior investigations, we found that a composition containing 50% PLGA with a L/G ratio of 75/25 suspended with NMP, when injected into animals cause some irritable reactions and some difficulty moving. Furthermore, the level of drug release with such an implant made with PLGA is not sufficient to prevent *Plasmodium* infection. With the rate of drug release from the implant containing 50% PLGA and 50% decoquinate, infectious diseases are not efficiently prevented. In our prior animal studies malaria *Plasmodium* is only partially prevented with the amount of decoquinate released by the implant containing PLGA. Attempts to adjust ratios of the drug active to the PLGA in making implants to prevent malarial infection were not successful.

The present invention provides prophylactic and therapeutic implants using naturally available materials that are easily metabolized or degraded or excreted by animals or humans. Therefore, surgical removal of the implants can be avoided. Also, the pain and distress associated with the irritation of placing the implant can be reduced. The methods of drug delivery of the present disclosure include implants comprising natural materials such as cholesterol and mono- and diglyceride as major components. These natural materials together with an anti-malarial compound such as decoquinate constitute implants having advantages over those utilizing polymers such as polylactic acid (PLA) or polyglycolic acid (PGA) or a copolymer (poly lactic-co-glycolic acid) (PLGA) or polycaprolactone (PCL) in preventing *Plasmodium* infection in mice. Furthermore, cholesterol and mono- or diglycerides are widely available natural materials and have been commonly used as food and medicinal ingredients.

The present invention provides implants that can be easily placed subcutaneously or intramuscularly in a patient to release a medication for a period ranging from at least 2 months to 6 months, which can further help solve the problem of non-compliance for a subject who has difficulty taking medications on a daily basis or more frequently.

SUMMARY OF THE INVENTION

Implants comprising the antimalarial agent decoquinate or a therapeutic drug are disclosed. In the preferred embodiment, the implants are in the form of a complex comprising a drug, a lipid or lipids and optionally a polymeric carrier. The present invention provides methods for preparing these implants wherein the implants comprise decoquinate or a therapeutic drug, cholesterol, monoglycerides, or diglycerides, and optionally a small percentage of a biocompatible polymer. These complexes are useful for releasing a therapeutic drug at a constant level and maintaining a prophylactic or therapeutic level of a drug in a subject, for preventing a malarial infection or treating diseases or disorders.

In another embodiment, the present invention provides methods of fabrication processes for the implant comprising a bioactive agent, a lipid or lipids such as cholesterol, or mono or diglycerides of medium chain fatty acids (Capmul MCM EP, Abitec, US), and optionally a polymer selected from polylactic acid (PLA) or polyglycolic acid (PGA) or poly (lactic-co-glycolic acid) (PLGA) or polycaprolactone (PCL). Components of the implants are blended with a mixer machine and subject to further mixing and extrusion through a hot melt extruder (HME) machine. The output materials from HME machine are solid in nature, but malleable, wherein the products can be formed into suitable in shapes and size dimensions for placement in animals or human bodies.

In another embodiment, the HME extruded implantable product is grinded into a powder form and suspended in saline for placement in patients by subcutaneous or intramuscular injection. The saline water phase upon injection is absorbed by surrounding tissues and the solid components remain in situ for slow and constant release of the prophylactic or therapeutic agent.

In another embodiment, each component of the implant can also be mixed together using organic solvents which can then be removed by evaporation. The remaining solid components can then be suspended in saline for placement in patient by subcutaneous or intramuscular injection.

In another embodiment, the implants can be placed in a subject without discomfort and remain in situ with no adverse effects. The implants in the present invention provide a controlled release of decoquinate, or the desired drug active, at a constant rate and maintain a sufficient level of decoquinate, or the desired drug active, in a subject for preventing a *Plasmodium* infection for a period over at least 2 months to as long as 6 months, or therapeutic level of the drug in a subject for treating diseases or disorders for a period over at least 2 months to as long as 6 months.

DESCRIPTION OF THE DRAWINGS

FIG. 1 shows a plot for the in vitro release of decoquinate. The release profile was determined by placing one gram of each sample of implants (F1, F2, F3, F4, and F5 that were prepared as described in Examples 1-5, respectively) in 40 ml of phosphate buffered saline (PBS) that was shaken at 80 rpm. Decoquinate was measured by HPLC analysis at the time points as indicated in the figure. The results show that the implant of formula F1 described in Example 1 has about 20% of the drug released on day 20 and about 35% on day 50. The drug release profiles for samples F2, F3, F4, and F5 are also shown.

FIG. 2 shows a schematic illustration for animal studies showing the experimental design for demonstrating prophylaxis against *Plasmodium* infection at the liver stage (i.e. the infection of liver cells). Briefly, at day 0, the liquid form of the compositions of the present invention at a dose of decoquinate 200 mg/kg were given by intramuscular injection or the implants of the present invention at a dose of decoquinate 200 mg/kg were placed by subcutaneous injection; mice were then inoculated with *Plasmodium berghei* ANKA 868 sporozites at week 6; next the in vivo image system (IVIS) images were taken at 24, 48 and 72 hours after the sporozoite inoculation; the parasitemia of each mouse was detected by microscopic visualization of blood smear every week (at weeks 7, 8, 9, and 10) after *Plasmodium* infection.

FIG. 3 shows data taken from the quantitative counting results of mouse experiments. Implants were placed in C57 mice by subcutaneous injection and remained in situ for 5 weeks. At week 6, the mice were inoculated by intravenous injection of 50,000 sporozoites of luciferase-expressing *Plasmodium berghei* ANKA 868. The results showed that the implant of formula F1 described in Example 1 is most effective in preventing *Plasmodium* infection after being placed in mice for 5 weeks. The vehicle includes the implant with the components for formula F1 without decoquinate. Primaquine is used as a positive control in the experiment. F7 is the implant of Example 7.

FIG. 4 shows data from the same experiment described as in FIG. 3. The results shown are the parasitemia detected 6 days after *Plasmodium berghei* ANKA sporozoite inoculation. Four out of five mice with the placement of implants of formula F1 described in Example 1 were free of *Plasmodium* infection and one out of five mice had a low level of parasitemia which was then disappeared 25 days after *Plasmodium* inoculation (shown in FIG. 5).

FIG. 5 shows that the detection of parasitemia continued for live mice up to 60 days. Except for mice having F1 implants, all mice infected with *Plasmodium* parasites died by day 30. One mouse implanted with the F1 implant showed parasite infection at blood stage that started at day 10, reached a peak level at day 15, and then vanished after day 25 after the inoculation, indicating the continuous release of decoquinate at days between 15 and 25 after the inoculation or the continuous release of decoquinate 70 days after the depot was implanted.

FIG. 6 shows the survival rate from the animal studies described as in FIG. 5. A group of 5 mice having implants F1 (described in Example 1) survived upon *Plasmodium* sporozoite inoculation. All mice in the vehicle control group, primaquine group and the F7 implant group died within 30 days of the sporozoite inoculation.

FIG. 7 show results from a separate experiment from the one as described in FIG. 2 through FIG. 6. For these experiments, mice were randomly divided into different groups with 5 in each group. The formulations described in this FIG. 7 sequentially are from Examples 9, 3, 1, 4 and 11, among which formulations F9, F3 and F1 were given by injection of liquid in saline which was prepared by grinding the IME extruded material and suspended in saline with stirring for 2 hours, F1 was also given by injecting the implants in solid form; F4 and F11 were also given as solid form. The schematic timeline was the same as described in FIG. 2. For these experiments, the parasites in groups of F9, F3 and F1 were not seen in the thin film so that thick films were prepared for all samples for detection of parasites and the results expressed as the parasite number per 100 white blood cells (WBC).

FIG. 8 shows the blood concentration of decoquinate (DQ) in nanograms per milliliter in mice dosed with the implant F3 (made in Example 3). The implant was given to C57 mice by intramuscular injection in liquid form at the dose of DQ 200 mg/kg body weight. The total injected volume was 200 μl with a 100 μl to each side of the hind legs. The blood samples were drawn at different time points (day 32, day 55, and day 92, respectively) by cardiac puncture and treated by the method described in the section of pharmacokinetic experiments as described herein.

DETAILED DESCRIPTION

The invention will now be described in detail with reference to exemplary embodiments, as illustrated in the accompanying figures. The description will address specific details in order to provide a thorough understanding of the invention. However, it will be apparent to one skilled in the art that the invention may be practiced without some or all of these specific details. In other circumstances, well-known features and/or process steps have not been described in detail in order to not unnecessarily obscure the key components of the present invention. The features and advantages of the invention will be described following the drawings and discussions that follow.

The invention is based in part on the discovery that incorporation of a practically insoluble small molecule with antimalarial activity in a depot vehicle in the physical form of a soft solid produces a small molecule drug formulation that has near zero-order release in vivo. The release profile shows minimal lag time and burst of drug delivery. For a depot formulation, this release profile is ideal in the case of preventing infectious diseases. It is surprising because the prevailing thought in the art is that a low burst, near zero-order release is only attainable with well-known polymers utilized in the formulation of the controlled release of a drug, such as injectable implants made of PLGA for zero-order release of drugs.

In one embodiment, the present invention provides an implant comprising decoquinate or a therapeutic agent in an amount of 10-40% by weight of the total implant, a cholesterol in an amount of 40-90% by weight of the total implant, a lipid in an amount of 5-20% by weight of the total implant, and optionally a polymer in an amount of 5-30% by weight of the total implant; the lipid comprising mono and diglycerides of medium chain fatty acids (Capmul MCM EP); the polymer is selected from polylactic acid (PLA) or polyglycolic acid (PGA) or poly (lactic-co-glycolic acid) (PLGA) or polycaprolactone (PCL). The copolymer used in the implant is PLGA 75:25 whose composition is 75% lactic acid and 25% glycolic acid based on the molar ratio of the monomers used for the polymerization. The addition of polymers is optional depending on the drug molecules and on the disease type wherein best clinical outcome can be achieved. An implant comprising decoquinate, cholesterol and Capmul MCM EP provides a sufficient level of decoquinate for at least two months in preventing malarial infection upon inoculation of *Plasmodium* sporozoites. In contrast, implants that are composed of only decoquinate and PLGA or PGA or PLA or PC are not sufficient to fully prevent malarial infection two months later upon the inoculation of *Plasmodium* sporozoites.

In another embodiment, the present invention provides a method of fabrication of the implant comprising decoquinate or an antimalarial drug or other therapeutic drugs, cholesterol, mono and diglycerides of medium chain fatty acids (Capmul MCM EP), and a polymer selected from polylactic acid (PLA) or polyglycolic acid (PGA) or poly (lactic-co-glycolic acid) (PLGA) or polycaprolactone (PCL). Components of the implant are blended using a mixer machine and then subjected to the process of hot melt extrusion (HME) through a hot melt extruder machine. The output materials from the HME machine are a soft solid in nature, i.e. a semi-solid, with changeable shape, i.e. malleable shape, wherein the products can be made suitable in shape and in quantitation for placement, i.e. implantation, in animals or human bodies.

In another embodiment, the present invention provides an implantable or injectable pharmaceutical composition, comprising: drug active particles comprising cholesterol; an ester selected from mono and diglycerides of medium chain fatty acids, and mixtures thereof; and an antiparasitic drug active, wherein the particles have an average particle size diameter range from 1.5 μm to 50 μm, and the composition is in the form of a viscous paste.

In another embodiment, the present invention provides a composition wherein the antiparasitic agent is selected from amprolium, arprinocid, artemether, clazuril, clopidol, decoquinate, diclazuril, dinitolmide, ethopabate, halofuginone, lasalocid, monensin, narasin, nicarbazin, oryzalin, ponazuril, robenidine, roxarsone, salinomycin, spiramycin, sulfadiazine, sulfadimethoxine, toltrazuril, triazuril (Tiazuril), and pharmaceutically acceptable salts and/or hydrates thereof, and mixtures of the foregoing.

In another embodiment, the present invention provides a composition wherein the antiparasitic agent is decoquinate, or a pharmaceutically acceptable salt and/or hydrate thereof.

In another embodiment, the present invention provides a composition wherein the antiparasitic agent is decoquinate in its free base form.

In another embodiment, the present invention provides a composition wherein the ester is selected from mono and diglycerides of caprylic acid, capric acid, and combinations thereof.

Preferably, the ester is glycerol monocaprylocaprate.

In another embodiment, the present invention provides a composition wherein the cholesterol is present in the formulation in an amount ranging from 40% to 90% by weight of the composition.

In another embodiment, the present invention provides a composition wherein the cholesterol has a melting point of 148-150° C.

In another embodiment, the present invention provides a composition wherein the ester is present in an amount ranging from 5% to 20% by weight of the composition.

In another embodiment, the present invention provides a composition wherein the ester has a number average molecular weight of 218-246 g/mol., melting point below 25° C. The number average molecular weight is preferably 218.29 g/mol.

In another embodiment, the present invention provides a composition wherein the decoquinate free base is present in the formulation in an amount ranging from 10% to 40% by weight of the composition.

In another embodiment, the present invention provides a composition wherein the decoquinate free base is present in the formulation in an amount ranging from 20% to 30% by weight of the composition.

In another embodiment, the present invention provides a composition further comprising a polymer selected from polylactic acid (PLA), polyglycolic acid (PGA), polycaprolactone (PCL), poly (lactic-co-glycolic acid) (PLGA), and combinations thereof.

In another embodiment, the present invention provides a composition wherein the polymer is selected from polylactic acid (PLA), polyglycolic acid (PGA), polycaprolactone (PCL), and combinations thereof, and is present in the composition in an amount ranging from 5% to 30% by weight of the composition.

In another embodiment, the present invention provides a composition wherein the polymer is selected from polylactic acid (PLA), polyglycolic acid (PGA), polycaprolactone (PCL), and combinations thereof, and is present in the composition in an amount ranging from 10% to 20% by weight of the composition.

In another embodiment, the present invention provides a composition wherein the copolymer is selected from poly (lactic-co-glycolic acid) or PLGA 75:25 whose composition is 75% lactic acid and 25% glycolic acid based on the molar ratio of the monomers comprising the copolymer.

In another embodiment, the present invention provides a composition wherein the copolymer is selected from poly (lactic-co-glycolic acid) or PLGA 75:25 and is present in the formulation in an amount ranging from 5% to 30% by weight of the composition.

In another embodiment, the present invention provides a composition wherein the copolymer is selected from poly (lactic-co-glycolic acid) or PLGA 75:25 and is present in the formulation in an amount ranging from 10% to 20% by weight of the composition.

In another embodiment, the present invention provides a composition wherein the cholesterol is present in an amount ranging from 40% to 90% by weight of the composition, the ester is present in an amount ranging from 5% to 20% by weight of the composition, the decoquinate free base is present in an amount ranging from 10% to 40% by weight of the composition, and the polylactic acid (PLA), polyglycolic acid (PGA), polycaprolactone (PCL), or poly(lactic-co-glycolic acid) is present in an amount ranging from 5% to 30% by weight of the composition.

In another embodiment, the present invention provides a process for making a composition wherein the components are mixed and processed in a hot melt extruder (HME) machine with a temperature range from 70° C. to 90° C. and a screw rotation speed range from 20 rpm to 100 rpm.

In another embodiment, the present invention provides a process wherein the screw rotation speed range is from 40 rpm to 80 rpm.

In another embodiment, the present invention provides a process wherein the output products of the components from the HME machine are mechanically manipulated into a shape, a size and an amount suitable for injection by a cannula for subcutaneous or intramuscular injection.

In another embodiment, the present invention provides a method for the prophylaxis or treatment of malaria in a mammal in need thereof comprising administering a therapeutically effective amount of a composition of the present invention to the mammal.

In another embodiment, the present invention provides a composition according to the present invention in the manufacture of a medicament for the prophylaxis or treatment of malaria in a mammal in need thereof.

Decoquinate and Other Antiparasitic Agents

The implantable or injectable pharmaceutical compositions of the present invention is comprise antiparasitic agents such as decoquinate, or mixtures of such agents.

Decoquinate (DQ), a (hydroxyl) quinoline, is produced by chemical synthesis. Its nomenclature is 4-hydroxyquinoline (ethyl-6-decyloxy-7-ethoxy-4-hydroxyquinoline-3-carboxylate) with CAS number 18507-89-6, molecular weight 418, and the molecular formula C25H35NO5). Decoquinate corresponds to the following chemical structure.

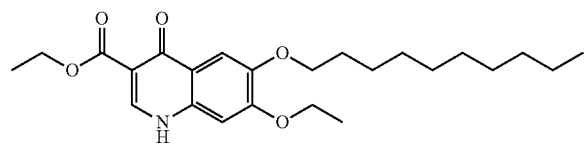 [SMILES: CCCCCCCCCCOc1cc2c(=O)c(C(=O)OCC)c[nH]c2cc1OCC]

As seen from the chemical structure, decoquinate has a secondary amine functionality and can be used or formulated in its free base form. Alternatively, pharmaceutically acceptable salts of decoquinate can be used, examples including the hydrochloride and hydrobromide salts, as well as sulfate and hydrogen sulfate salts. Also, the anhydrous and various hydrate forms of decoquinate and its salts are contemplated within the scope of the invention.

Decoquinate was shown to increase the activity of meticlorpindol (3, 5-Dichloro-2, 6-dimethyl-4-pyridinol) against malaria in a mammal [U.S. Pat. Nos. 4,031,220 and 4,195,089].

More recently, decoquinate itself has emerged as a potent in vitro and in vivo inhibitor of the *Plasmodium* parasite at the infection of the liver stage in mammals and acts by selectively and specifically inhibiting the parasite's mitochondrial bc1 complex, with little cross-resistance with its analog atovaquone, an existing antimalarial drug on market. After administration of decoquinate to *P. yoelii* infected animals in a corn oil emulsion, decoquinate was shown to be efficacious in causal prophylaxis of parasitemia at 50 mg/kg [Tae-gyu Nam et al (2011) A chemical genomic analysis of decoquinate, a *Plasmodium falciparum* Cytochrome b inhibitor, *ACS Chemical Biology* 6 (11): 1214-1222]. More recently, a single dose of 5 mg/kg of decoquinate suspended in soybean oil was shown to prevent the appearance of blood stage *Plasmodium berghei* ANKA parasites in infected mice [Filipa. P. da Cruz. et al (2012) Drug screens targeted at *Plasmodium* liver stages have shown it to be a potent multistage antimalarial drug, Journal of Infectious Diseases 205(8):1278-86].

Decoquinate has been used as a coccidiostat for many years without any known adverse effects [U.S. Pat. No. 3,485,845, 1969]. The agricultural/veterinary product sold under the trade name Deccox® (Rhone-Poulenc) contains 6% decoquinate in Feed Additive with corn meal, soybean oil, lecithin and silicon dioxide and used in cattle, goats and poultry under the protection of patents [U.S. Pat. No. 3,485,845 1969 and U.S. Pat. No. 3,544,686 1970]. It acts on the sporozoite stage of the life cycle. The mechanism of action is thought to be the inhibition of electron transport and respiration of the parasite's mitochondrial respiratory chain [Fry M. et al (1984) Effects of decoquinate and clopidol on electron transport in mitochondria of *Eimeria tenella* (Apicomplexa: *Coccidia*), Biochemical Pharmacology 33 (2): 229-40]. Decoquinate has also been shown to ameliorate the symptoms of cryptosporidiosis such as diarrhea if used in effective amounts in susceptible host animals [U.S. Pat. No. 5,200,418, 1993].

Nanoparticle formulations of decoquinate have been shown to increase the bioavailability and antimalarial efficacy due to the increase of surface area of the formulation particles and have been shown to be increase the water solubility of the compound. (Hongxing Wang et, al. Formulation and Particle Size Reduction Improve Bioavailability of Poorly Water-Soluble Compounds with Antimalarial Activity, Malaria Research and Treatment, Volume 2013 Article ID 76923; Hongxing Wang et, al. Nanoparticle formulations of decoquinate increase antimalarial efficacy against liver stage *Plasmodium* infections in mice, Nanomedicine: Nanotechnology, Biology, and Medicine, 10 (2014) 57-65). Although these efforts to improve the activity of decoquinate against malarial *Plasmodium* can be used for dosing the agent via oral administration or via an intravenous route of administration, a controlled release of the compound when incorporated into an implant is a different approach of drug administration and does not require nano- or fine particles. In fact, nano-sized particles are much less effective in prophylaxis of *Plasmodium* infection [Qigui Li, Lisa Xie, Diana Caridha, et al (2017) Long-Term Prophylaxis and Pharmacokinetic Evaluation of Intramuscular Nano- and Microparticle Decoquinate in Mice Infected with *P. berghei* ANKA Sporozoites, Malaria Research and Treatment, Volume 2017, Article ID 7508291, 10 pages].

Other antiparasitic agents useful herein include: amprolium, arprinocid, artemether, clazuril, clopidol, diclazuril, dinitolmide, ethopabate, halofuginone, lasalocid, monensin, narasin, nicarbazin, oryzalin, ponazuril, robenidine, roxarsone, salinomycin, spiramycin, sulfadiazine, sulfadimethoxine, toltrazuril, and triazuril (Tiazuril), as well as various pharmaceutically acceptable salt and/or hydrate forms of these agents. Also, combinations of antiparasitic agents are contemplated herein.

Cholesterol

The implantable or injectable pharmaceutical compositions of the present invention comprise cholesterol. Cholesterol is an organic molecule that composes about 30% of all animal cell membranes. It is an essential structural component of all animal cell membranes and is essential to maintain both membrane structural integrity and fluidity. The membrane remains stable and durable without being rigid, allowing animal cells to change shape and the animals to move. In addition to its importance for animal cell structure, cholesterol also serves as a precursor for the biosynthesis of steroid hormones, bile acid, and vitamin D. Because cholesterol is a biological substance and considered to be safe, it has been used in the application of drug formulations, mostly in lipid containing formulations such as liposomes. Although abnormal cholesterol levels such as higher blood LDL, especially higher LDL particle concentrations and smaller LDL particle sizes, contribute to myocardial infarction (heart attack), stroke, and peripheral vascular disease more than the cholesterol content of the HDL particles, there has been no evidence showing that the amount of cholesterol used in the drug formulation is associated with an increased risk of cardiovascular disease, given the fact that the pool size of cholesterol in the human body is proportionally so large and the metabolic route of cholesterol is so complex that the amount of cholesterol used in the drug formulation may not play a role beyond controlling implant drug release.

On the other hand, since cholesterol has the structure of the tetracyclic ring in a trans conformation, it makes all but the side chain of cholesterol rigid and planar. In this structural role, cholesterol also reduces the permeability of the plasma membrane to neutral solutes, hydrogen ions, and sodium ions. It is possible that this feature of cholesterol makes it suitable and valuable for its role within the implants to control the release of antimalarial agents as well as the release of other therapeutic drugs.

Mono- and Diglycerides of Medium Chain Fatty Acids

The implantable or injectable pharmaceutical compositions of the present invention comprise a mono- or diglyceride of medium chain fatty acids, or combinations of these mono- or diglycerides. The term of "medium chain fatty acids" refers to fatty acids having 6-12 carbon atoms. Preferably, the medium chain fatty acids have 8-10 carbon atoms. More preferably, the mono- or diglyceride of medium chain fatty acids used in the present invention are mono and diglycerides of caprylic acid, capric acid. One example of them is glycerol monocaprylocaprate. Capmul MCM EP is composed of mono and diglyceride of medium chain fatty acids (mainly caprylic). It is a useful solvent for many organic compounds, including steroids. It is also a useful emulsifier for water-oil systems. Although no reported information has been found indicating its use in the controlled release of therapeutic drugs, it is used in combination with cholesterol to form an implant comprising decoquinate in the present invention that has an excellent effect in *Plasmodium* prevention. In contrast, an implant containing only cholesterol and decoquinate has been shown to have quite different physical properties when processed in HME. Capmul MCM EP, an oily substance, may act as a "glue" or "adhering matrix" or "solubility enhancer" for the implants.

Captex® 300 is composed of medium-chain triglycerides. It can be used to enhance infiltration and bioavailability. In the formulation F10 was, however, not as effective as F1 in animal experiment for testing antimalaria infection (data not shown).

Polymers

In some embodiments, the implantable or injectable pharmaceutical compositions of the present invention can further comprise a polymer or copolymer derived from carboxylic acids and lactones. Generally, these polymeric materials are biodegradable, thermoplastic polyesters. Examples of such polymers include: polylactic acid (PLA), polyglycolic acid (PGA), polycaprolactone (PCL), poly (lactic-co-glycolic acid) (PLGA), and combinations thereof.

Preparation Methods

In the preparation of the implant comprising decoquinate, the temperature settings in the HME machine are based on the melting point and glass transition temperature of the components included in the formulation, and are generally below 100° C., preferably ranging from 70° C. to 90° C. The screw rotation speed of the machine is typically set at 20-100 rpm or preferably 40-80 rpm. The melting point of decoquinate is 242 to 246° C. The temperature settings in the present invention allow all ingredients, including active and inactive ingredients, to remain intact without decomposition. The temperature settings also allow the ingredients to be homogeneously mixed and physically adhered to each other, presumably through the oily substance mono and diglycerides. Alternatively, this process, however, is not necessarily hot melting. Also, alternatively, the decoquinate or other drugs are not necessarily mixed with the excipients in the molecular state during the extrusion process.

In another embodiment, the HME extruded implantable product is grinded into a powder form and suspended in saline for placement in patients by subcutaneous or intramuscular injection. The saline water phase upon injection is absorbed by surrounding tissues and the solid components remain in situ for slow and constant release of prophylactic or therapeutic agents.

In another embodiment, each component of the implant can also be mixed together using organic solvents which can then be removed by evaporation, and the solid components can be suspended in saline for placement in a patient by subcutaneous or intramuscular injection.

Methods of Treatment and Prophylaxis

The implantable or injectable pharmaceutical compositions of the present invention are useful for the treatment or prophylaxis of parasitic diseases in mammals such as malaria. These compositions are useful for providing treatment by delivering an effective dosage of the drug active for at least one month and for providing prophylaxis by delivering an effective dosage of the drug active for at least two months. It is known from the scientific literature that the minimum inhibitory concentration (MIC) for decoquinate for *Plasmodium* is 5.12 ng/ml. (See Qigui Lie et al., Long-Term Prophylaxis and Pharmacokinetic Evaluation of Intramuscular Nano- and Microparticle Decoquinate in Mice Infected with *P. berghei* Sporozites, Malaria Research and Treatment, Volume 2017, Article ID 7508291, 10 pages.) The compositions of the present invention can provide levels of decoquinate above this MIC level for 92 days or longer. Therefore, the compositions of the present invention can in be effective for treatment or prophylaxis for as long as about 90 days, or three months.

In another embodiment, the present invention provides a method of maintaining a prophylactic level of decoquinate or an antimalarial drug in a subject for a period over at least two months, comprising implants injectable to a subject, the implants comprising one or more individual biodegradable implants comprising (1) decoquinate or an antimalarial drug present in an amount of 10-40% by weight, relative to the weight of the implant; (2) a cholesterol present in an amount of 40-90% by weight, relative to the weight of the total implant, the cholesterol is a natural product and also a biocompatible substance used for controlled release of antimalarial agent in the present invention; (3) a lipid present in an amount of 5-20% by weight, relative to the weight of the total implant; the lipid is preferably mono and diglycerides of medium chain fatty acids (Capmul MCM EP), for example, mono and diglycerides of caprylic acid, capric acid; and (4) optionally a polymer or copolymer present in an amount of 5-30% by weight, relative to the weight of the total implant; the polymer comprising polylactic acid (PLA) or polyglycolic acid (PGA) or polycaprolactone (PCL); the copolymer comprising 75% poly lactic acid and 25% poly glycolic acid (PLGA 75:25) of the copolymer wherein the individual biodegradable implants, if more than one in number, do not differ significantly from one another in the molar ratio of lactic acid to glycolic acid. Therefore, implants of the present invention maintain a prophylactic level of decoquinate or an antimalarial agent in a subject for a period of at least two months, preventing *Plasmodium* parasite infection.

In another embodiment, the present invention provides a method of maintaining a therapeutic level of a drug in a subject for a period over at least one month, comprising implants injectable to a subject; the implants comprising one or more individual biodegradable implants comprising (1) a therapeutic drug present in an amount of 10-40% by weight, relative to the weight of the total implant; (2) a cholesterol present in an amount of 30-70% by weight, relative to the weight of the total implant, the cholesterol is a natural product and also a biocompatible substance used for controlled release of the drug in the present invention; (3) a lipid present in an amount of 5-20% by weight, relative to the weight of the total implant, the lipid is preferably mono and diglycerides of medium chain fatty acids (Capmul MCM EP), for example, mono and diglycerides of caprylic acid, capric acid; and (4) optionally a polymer or copolymer present in an amount of 5-30% by weight, relative to the weight of the total implant; the polymer comprising polylactic acid (PLA) or polyglycolic acid (PGA) or polycaprolactone (PCL); the copolymer comprising 75% poly lactic acid and 25% poly glycolic acid (PLGA 75:25) of the copolymer wherein the individual biodegradable implants, if more than one in number, do not differ significantly from one another in the molar ratio of lactic acid to glycolic acid. Therefore, implants of the present invention maintain a therapeutic level of the drug or drugs in a subject for a period of at least one month, treating diseases or disorders.

EXAMPLES

The following examples further describe and demonstrate embodiments within the scope of the present invention. The Examples are given solely for purpose of illustration and are not to be construed as limitations of the present invention, as many variations thereof are possible without departing from the spirit and scope of the invention.

The formulations F1, F2, F3, F4 and F5 described herein are designated accordingly from Examples 1, 2, 3, 4 and 5. Table 1, below provides the compositions for the formulations of Examples 1, 2, 3, 4, and 5.

TABLE 1

| Formulation | Chol (g) | MCM (g) | PLGA (g) | DQ (g) | Drug Load (%) |
| --- | --- | --- | --- | --- | --- |
| F1 | 52.50 | 7.50 | — | 15.00 | 20 |
| F2 | 45.00 | 7.50 | — | 22.50 | 30 |
| F3 | 37.50 | 7.50 | — | 30.00 | 40 |

TABLE 1-continued

| Formulation | Chol (g) | MCM (g) | PLGA (g) | DQ (g) | Drug Load (%) |
| --- | --- | --- | --- | --- | --- |
| F4 | 37.50 | 7.50 | 7.50 | 22.50 | 30 |
| F5 | 37.50 | 3.75 | 11.25 | 22.50 | 30 |

Note:
Chol = cholesterol:
MCM = Capmul MCM 8:
DQ = decoquinate:
PLGA: L-lactide-co-glycolide with L/G ratio of 75/25:

Example 1

Weigh 52.5 g cholesterol, 7.5 g MCM (Capmul MCM EP) (glycerol monocaprylocaprate (type I)) and 15.0 g decoquinate (Genebest, Zhejiang), mix well and wait until the actual temperature reaches the setting temperature in the HME machine (Pharma 11 HME, Thermo Fisher Scientific). The mixed material was added to the hopper and fed to the HME. The temperature for the extrusion process ranged from 70° C. to 90° C., and the tween screw speed ranged from 20 rpm to 50 rpm. The extruded material was either made as a solid stick of exact length for subcutaneous implantation or pulverized into a powder and then suspended in saline for intramuscular injection. The product was then tested for the in vitro release of the active decoquinate component. The implant was suspended in a water phase and particle size was measured to be between 1.5 µM and 50 µM.

Example 2

Weigh 45.0 g cholesterol, 7.5 g MCM (Capmul MCM EP) (glycerol monocaprylocaprate (type I)) and 22.5 g decoquinate, mix well and wait until the actual temperature reaches the setting temperature in the IME machine (Pharma 11 HME). The mixed material was added to the hopper and fed to the HME. The temperature for the extrusion process ranged from 70° C. to 90° C., and the tween screw speed ranged from 20 rpm to 50 rpm. The extruded material was either made as a solid stick of exact length for subcutaneous implantation or pulverized into a powder and then suspended in saline for intramuscular injection. The product was then tested for the in vitro release of the active decoquinate component. The implant was suspended in a water phase and particle size was measured to be between 1.5 µM and 50 µM.

Example 3

Weigh 37.5 g cholesterol, 7.5 g MCM (Capmul MCM EP) (glycerol monocaprylocaprate (type I)) and 30.0 g decoquinate, mix well and wait until the actual temperature reaches the setting temperature in the HME machine (Pharma 11 HME). The mixed material was added to the hopper and fed to the HME. The temperature for the extrusion process ranged from 70° C. to 90° C., and the tween screw speed ranged from 20 rpm to 50 rpm. The extruded material was either made as a solid stick of exact length for subcutaneous implantation or pulverized into a powder and then suspended in saline for intramuscular injection. The product was then tested for the in vitro release of the active decoquinate component. The implant was suspended in a water phase and particle size was measured to be between 1.5 µM and 50 µM.

Example 4

Weigh 22.5 g cholesterol, 7.5 g MCM (Capmul MCM EP) (glycerol monocaprylocaprate (type I)), 7.5 g PLGA 75/25, and 22.5 g decoquinate, mix well and wait until the actual temperature reaches the setting temperature in the HME machine (Pharma 11 HME). The mixed material was added to the hopper and fed to the HME. The temperature for the extrusion process ranged from 70° C. to 90° C., and the tween screw speed ranged from 20 rpm to 50 rpm. The extruded material was either made as a solid stick of exact length for subcutaneous implantation or pulverized into a powder and then suspended in saline for intramuscular injection. The product was then tested for the in vitro release of the active decoquinate component. The implant was suspended in a water phase and particle size was measured to be between 1.5 µM and 50 µM.

Example 5

Weigh 37.5 g cholesterol, 3.75 g MCM (Capmul MCM EP) (glycerol monocaprylocaprate (type I)), 11.25 g PLGA 75/25, and 22.5 g decoquinate, mix well and wait until the actual temperature reaches the setting temperature in the HME machine (Pharma 11 HME). The mixed material was added to the hopper and fed to the HME. The temperature for the extrusion process ranged from 70° C. to 90° C., and the tween screw speed ranged from 20 rpm to 50 rpm. The extruded material was either made as a solid stick of exact length for subcutaneous implantation or pulverized into a powder and then suspended in saline for intramuscular injection. The product was then tested for the in vitro release of the active decoquinate component. The implant was suspended in a water phase and particle size was measured to be between 1.5 µM and 50 µM.

Example 6

Weigh 7.5 g PCL (polycaprolactone 45000), 37.5 g PEG (poly ethylene glycol) 6000, and 30 g decoquinate, mix well and wait until the actual temperature reaches the setting temperature in the HME machine (Pharma 11 HME), The mixed material was added to the hopper and fed to the HME. The temperature for the extrusion process ranged from 60° C. to 80° C., and the tween screw speed ranged from 20 rpm to 50 rpm. The extruded material was either made as a solid stick of exact length for subcutaneous implantation or pulverized into a powder and then suspended in saline for intramuscular injection. The product was then tested for the in vitro release of the active decoquinate component. The implant was suspended in a water phase and particle size was measured to be between 1.5 µM and 50 µM.

Example 7

Weigh 575 mg PLGA 75/25 and 575 mg decoquinate. PLGA was first dissolved in N-methyl-2-pyrrolidone (NMP), and then decoquinate added to the PLGA solution. The mixture was stirred for 2 hours at 200 rpm at room temperature. The mixture solidified and was tested for the in vitro release of the active decoquinate component.

Example 8

Weigh 1.2 g PLGA 50/50 and 1.2 g decoquinate. PLGA was first dissolved in N-methyl-2-pyrrolidone (NMP), and then decoquinate added to the PLGA solution. The mixture was stirred for 2 hours at 200 rpm at room temperature. The mixture solidified and was tested for the in vitro release of the active decoquinate component.

Example 9

Weigh 42 g cholesterol and 18 g decoquinate, mix well and wait until the actual temperature reaches the setting temperature in the HME machine (Pharma 11 HME). The mixed material was added to the hopper and fed to the HME. The temperature for the extrusion process ranged from 80° C. to 140° C., and the tween screw speed ranged from 20 rpm to 50 rpm. The extruded material was either made as a solid stick of exact length for subcutaneous implantation or pulverized into a powder and then suspended in saline for intramuscular injection. The product was then tested for the in vitro release of the active decoquinate component. The implant was also suspended in a water phase and particle size was measured to be between 1.5 µM and 50 µM.

Example 10

Weigh 0.375 cholesterol, 0.5 g decoquinate and 25 ml Captex 300 (medium-chain triglycerides). The components are added together, heated at 80° C. degree, and mixed with stirring. The formulation was directly used as a depot by subcutaneous injection.

Example 11

Weigh 50.04 g cholesterol, 6.0 g MCM (Capmul MCM EP) (glycerol monocaprylocaprate (type I)), mix well and wait until the actual temperature reaches the setting temperature in the HME machine (Pharma 11 HME). The mixed material was added to the hopper and fed to the HME. The temperature for the extrusion process ranged from 80° C. to 140° C., and the tween screw speed ranged from 20 rpm to 50 rpm. The extruded material was made as a solid stick of exact length for subcutaneous implantation as a vehicle control.

Drug Release Test

Drug release tests were carried out by placing the weighed implant in phosphate buffered saline (PBS) buffer PH 7.4 with rotation shaking at speed of 100 rpm. Samples were taken as indicated in FIG. 1 and the drug concentration was measured by HPLC analysis (Agilent) and compared to the total amount of the drug concentration that was measured. The results showed that by 50 days the formulations F1 to F3 (Examples 1-3) demonstrated a drug release ranging from 25% to 35%. The formulations F4 and F5 (Examples 4 and 5) demonstrated only about 5% drug release by 50 days.

Animal Studies

The implants made in Examples 1, 7, along with a vehicle control, and primaquine as a control were evaluated in an animal model developed in the inventors' laboratory. The animal studies were carried out in strict accordance with the relevant animal testing regulations (Animal Management Regulations, PR China, issued on Nov. 14, 1088, revised version on Mar. 1, 2017). The implants having 200 mg/kg body weight of the active drug to be evaluated were placed subcutaneously in C57 mice 6 weeks prior to sporozoite inoculation by *Plasmodium beighei* ANKA (Pb 868 sporozoites) expressing firefly luciferase. The sporozoites were given to the mice by intravenous injection of approximately 50,000 sporozoites isolated from the salivary glands of female *Anopheles stephensi* mosquitoes infected with *Plas-*

*modium berghei*. Each testing group was randomly selected to have five mice. Each animal study was repeated at least three times.

Figure 2:
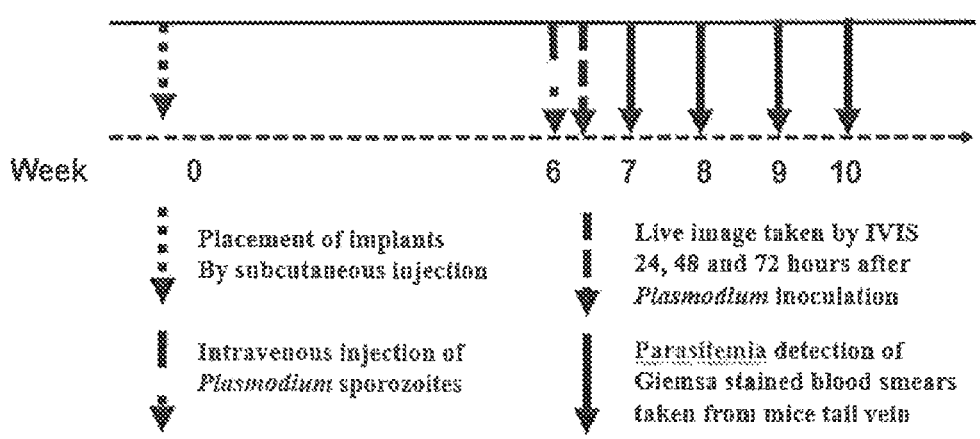
Figure 3:
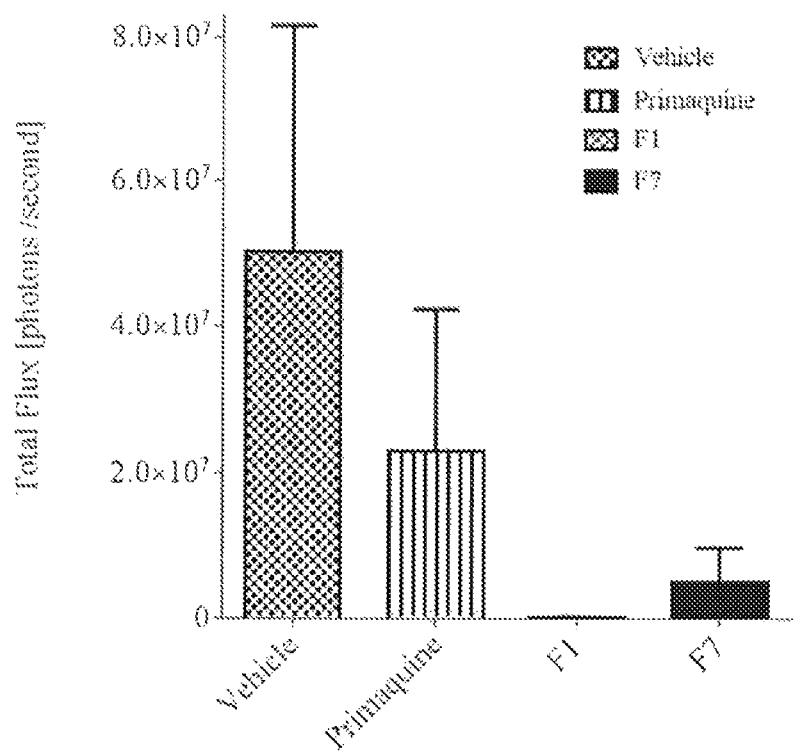
Figure 4:
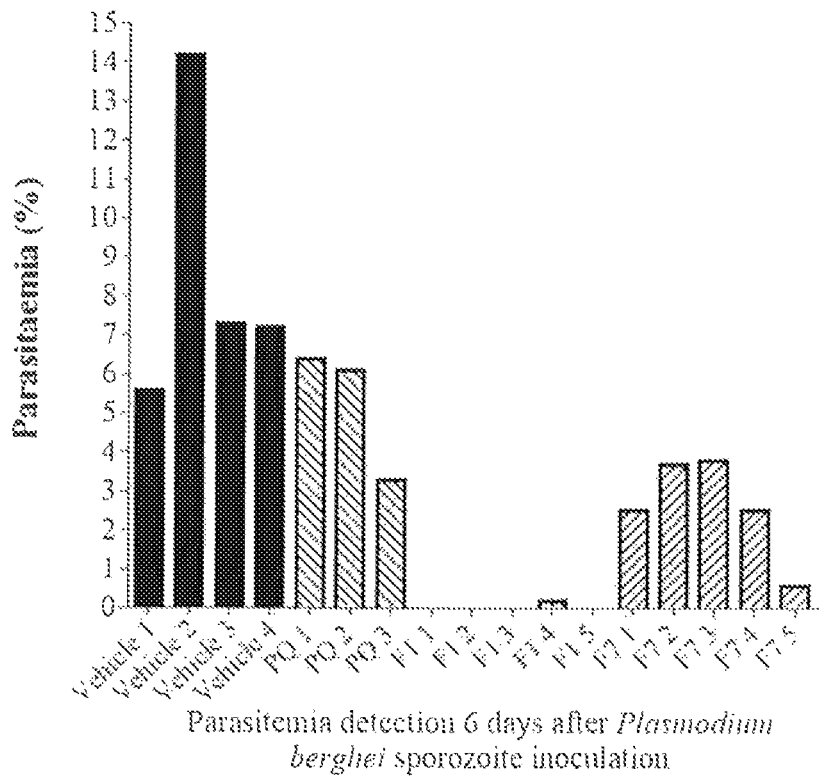
Figure 5:
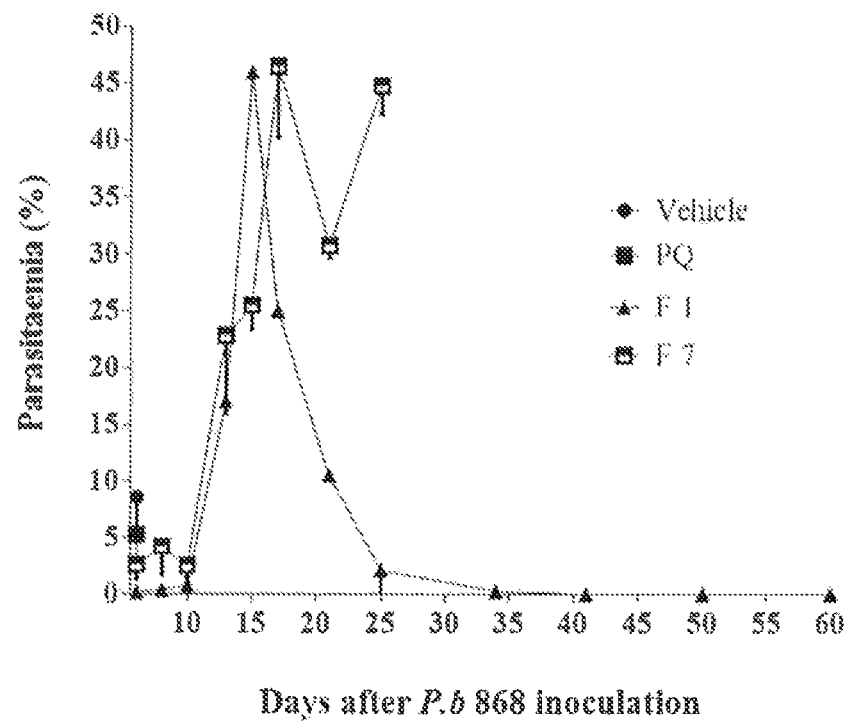
Figure 6:
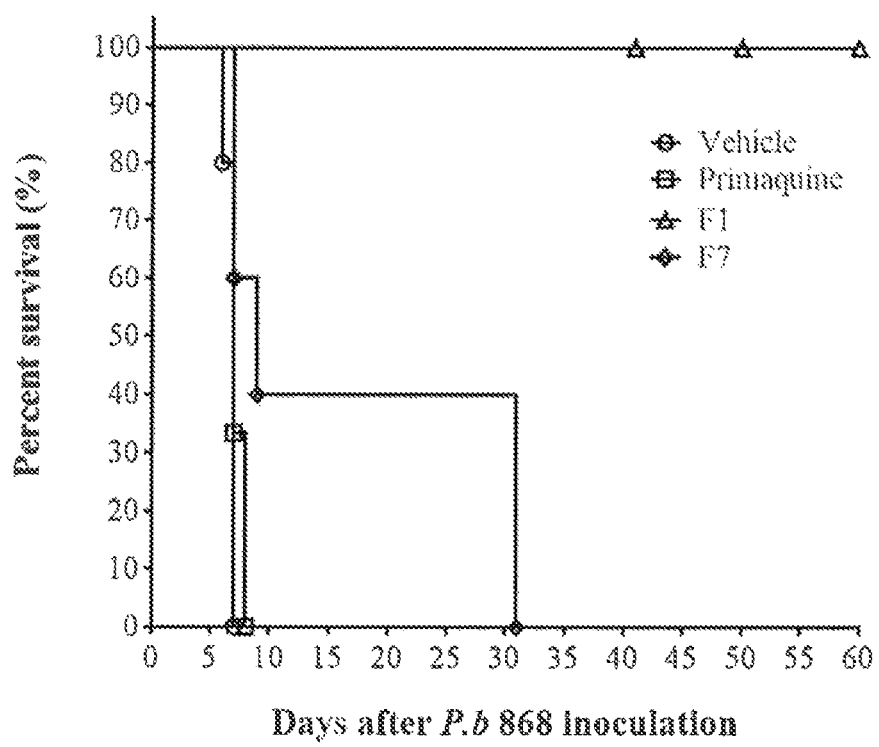
Figure 7:
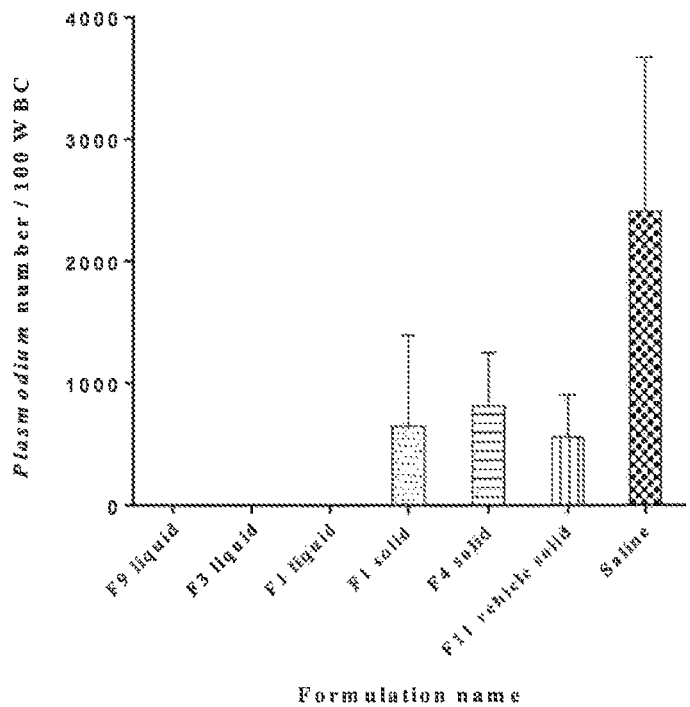
Figure 8:
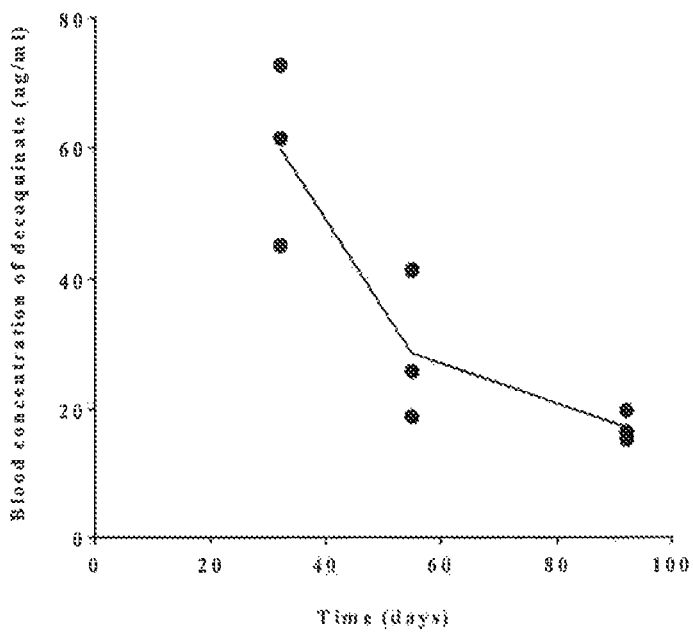

The prophylactic effect on suppressing infection of luciferase-expressing *Plasmodium beighei* 868 was observed during a time course of 10 weeks in C57 mice upon *P. beighei* sporozoite inoculation. The sporozoite development at the liver stage was monitored by live image detection using a caliper spectrum in vivo imaging system (IVIS). Parasitemia measurements were performed by microscopical visualization of the parasite number in the infected blood cells from Giemsa stained blood smears. A thin film of blood was prepared and stained with 3% Giemsa for 20 minutes; and then the number of infected red blood cells per 10,000 red blood cells was counted under an oil microscope to obtain an erythrocyte infection rate (standard method for thin film of blood is either the number of infected red blood cells per 10,000 red blood cells or the number of infected red blood cells per 1000 red blood cells—generally the former is used herein). In the case that the parasites were not seen on the slides, a thick film was prepared and stained with 3% Giemsa for 20 minutes; and then the number of infected red blood cells per 100 white blood cells (WBC) was counted and expressed as the number of *Plasmodium* cells per 100 WBC. Survival rates were calculated based on day 90 after the implant placement. The schematic depiction of the experimental design is shown on FIG. 2.

Sporozoite Isolation and Inoculation

*P. berghei* ANKA luciferase-expressing sporozoites were obtained from laboratory-reared female *Anopheles stephensi* mosquitoes from the Guangzhou CAS-Lamvac Biotech. Co. The mosquitoes were maintained at 26° C. for 17 to 22 days after feeding on *Plasmodium* parasites from infected Kunming mice (adapted from Swiss mice). Salivary glands were extracted from malaria-infected mosquitoes that were separated into abdomen and head/thorax regions. Heads and thoraxes were triturated with a mortar and pestle and suspended in medium RPMI 1640 containing 1% C57 mouse serum. A total of 50-80 heads with glands were placed into an Osaki tube on top of glass wool in the 0.5 ml tube with enough dissection media to cover the heads. The Osaki tube was kept on ice until all the mosquitoes had been dissected. Sporozoites were recovered and isolated from the salivary glands. Each mouse was inoculated intravenously in the tail vein with approximately 50,000 sporozoites suspended in 0.1 ml volume on day 0.

In Vivo Image System (IVIS)

In vivo imaging of bioluminescence activity from luciferase-expressing *P. berghei* ANKA infected mice were performed using an IVIS Spectrum (Caliper, PerkinElmer). Mice were evaluated at 24, 48, and 72 hours post sporozoite inoculation to determine liver- and blood-stage malarial infections. Mice received 150 mg/kg luciferin (Gold Biotechnology, St. Louis, Mo.) intraperitoneally in a volume not exceeding 150 µl. Three minutes post luciferin administration; the mice were anesthetized with inhaled isoflurane. The mice were then positioned ventral side up in the IVIS on a 37° C. platform. The mice continued to receive isoflurane through a nose cone delivery. The camera exposure times utilized were 1 and 5 minutes for the 24, 48, and 72-hour time points with f-stop=1 and a large binning setting. Quantitative analysis measuring bioluminescent photons emitted from whole bodies or regions of intensity (ROI) were performed by measuring the luminescence signal intensity using the ROI settings of the Living Image® 4.0 software. The ROI assessment, which measures the total flux of photons in an anatomic location, was set to measure the abdominal area at the location of the liver from whole body imaging. A 3-D bioluminescent imaging tomography was performed with the software using sequential images taken with filters ranging from 580 to 660 nm.

Toxicity Assessment of Decoquinate Implants

Varying doses of decoquinate (200 mg/kg) based on quantification from an HPLC assay in each preparation was administrated subcutaneously to the mice. The immediate toxicity was observed, and chronic adverse effects were continued to be observed for 14 days. All animals survived at the end of the observation. The general observations included circling in cages, depression, head tilt, hunched posture, observation of blood (cage/urine/hair), dehydration, diarrhea, weight loss, hair loss (Barbering), skin lesions, limping, not eating and vomiting. Animals with implants comprising only PLGA and decoquinate showed some distress right after the implant injection and difficult moving. None of the animals with implants comprising cholesterol, Campul MCM EP and decoquinate showed any of the signs described above. Other signs which were not observed in any of the animals dosed with varying amounts of decoquinate included: d ataxia, deep breathing, convulsions, diarrhea, epistaxis, hematuria, jaundice, lameness or limping, marasmus, melena, nodule development.

Pharmacokinetic Experiments

Chromatographic analyses by using LC-10ADvp HPLC system (SHIMADZU, Japan), MPS3C automatic sampler (Gerstel Auto sampler, Germany) and API3000 triple quadrupole tandem mass spectrometer (AB-SCIEX co., U.S.) were performed. Decoquinate standard (Cat. No. 1165408, LOT F0G036) was from USP Rockville, Md., USA. Propranolol (≥95% in purity, Sigma Chemical Co.) was chosen as the internal standard. All chemicals and solvents were analytical grade. Water for the experiment was purified using a Millipore (AK, USA) laboratory ultra-pure water system (0.2 µm filter).

The compound was dissolved in ethanol at a concentration of 50 µg/ml and diluted with ethanol to a series of concentrations, and then 20 µl of each concentration solution and 100 µl blank blood were added to 1.5 ml tube and vortex for 3 min, then 400 µl ethanol acetonitrile containing internal standard were added and vortex for 5 min. After standing at room temperature for 8 hours, vortex for 5 min, finally spin tubes in centrifuge at 16000 g for 60 min at 4° C. Final concentrations were as follows: 0.5, 1, 2, 5, 10, 20, 50, 100, 200, 500 ng/ml.

The blood samples were prepared using protein precipitation method. Ethanol/acetonitrile (1:1) was used as protein precipitation reagent. To each 1.5 ml tube 20 µl ethanol and 100 µl blood samples were added and vortex for 3 min, then 400 µl of protein precipitation solution containing internal standard were added and vortex for 5 min. The rest of procedures was the same as standard curve preparation. Subsequently, 100 µl of the supernatant was taken and placed into the 96 well plate and analyzed by a LC/MS/MS System (Applied Biosystems-Sciex model for API 3000 mass spectrometer).

The samples for quality control were at three different levels representing low, middle and high concentrations of DQ. The chromatographic column was Agilent ZORBAX Eclipse Plus C8 (2.1*50 mm, 3.5-Micron). The mobile phase consisted of 0.1% formic acid in methanol: 0.1% formic acid in water (90:10: v/v) at a flow rate of 600 µl/min. The column temperature was 30° C. and the temperature of injector 15° C.

INCORPORATION BY REFERENCE

The entire disclosure of each of the patent documents, including certificates of correction, patent application documents, scientific articles, governmental reports, websites, and other references referred to herein is incorporated by reference herein in its entirety for all purposes. In case of a conflict in terminology, the present specification controls.

EQUIVALENTS

The invention can be embodied in other specific forms without departing from the spirit or essential characteristics thereof. The foregoing embodiments are to be considered in all respects illustrative rather than limiting on the invention described herein. In the various embodiments of the present invention, where the term comprises is used, it is also contemplated that the embodiments consist essentially of, or consist of, the recited steps or components. Furthermore, the order of steps or the order for performing certain actions is immaterial as long as the invention remains operable. Moreover, two or more steps or actions can be conducted simultaneously.

In the specification, the singular forms also include the plural forms, unless the context clearly dictates otherwise. Unless defined otherwise, all technical and scientific terms used herein have the same meaning as commonly understood by one of ordinary skill in the art to which this invention belongs. In the case of conflict, the present specification will control.

The invention claimed is:

1. An implantable or injectable pharmaceutical composition, comprising:
    drug active particles comprising cholesterol;
    an ester selected from mono and diglycerides of medium chain fatty acids, and mixtures thereof; and
    an antiparasitic drug active,
    wherein the particles have an average particle size diameter range from 1.5 μM to 50 μM, and the composition is in the form of a viscous paste,
    and further comprising:
    a polymer selected from the group consisting of polylactic acid (PLA), polyglycolic acid (PGA), polycaprolactone (PCL), poly (lactic-co-glycolic acid) (PLGA), and combinations thereof,
    wherein the cholesterol is present in an amount ranging from 40% to 90% by weight of the composition,
    the ester is present in an amount ranging from 5% to 20% by weight of the composition,
    the antiparasitic drug active is present in an amount ranging from 10% to 40% by weight of the composition, and
    the polymer is present in an amount ranging from 5% to 30% by weight of the composition,
    and wherein the composition is prepared via hot melt extrusion.

2. A composition according to claim 1 wherein the antiparasitic agent is selected from the group consisting of amprolium, arprinocid, artemether, clazuril, clopidol, decoquinate, diclazuril, dinitolmide, ethopabate, halofuginone, lasalocid, monensin, narasin, nicarbazin, oryzalin, ponazuril, robenidine, roxarsone, salinomycin, spiramycin, sulfadiazine, sulfadimethoxine, toltrazuril and triazuril, and pharmaceutically acceptable salts and/or hydrates thereof, and mixtures of the foregoing.

3. A composition according to claim 2 wherein the antiparasitic agent is decoquinate, or a pharmaceutically acceptable salt or hydrate thereof.

4. A composition according to claim 2 wherein the antiparasitic agent is decoquinate in its free base form.

5. A composition according to claim 3, wherein the ester is selected from the group consisting of mono and diglycerides of caprylic acid, capric acid, and combinations thereof.

6. The composition of claim 5, wherein the cholesterol has a melting point of 148-150° C.

7. The composition of claim 5, wherein the ester has a number average molecular weight of 218-246 g/mol, melting point below 25° C.

8. The composition of claim 4, wherein the decoquinate free base is present in the formulation in an amount ranging from 10% to 40% by weight of the composition.

9. The composition of claim 4, wherein the decoquinate free base is present in the formulation in an amount ranging from 20% to 30% by weight of the composition.

10. The composition of claim 5, wherein the polymer is selected from the group consisting of polylactic acid (PLA), polyglycolic acid (PGA) and polycaprolactone (PCL), and combinations thereof, and is present in the composition in an amount ranging from 10% to 20% by weight of the composition.

11. The composition of claim 1, wherein the polymer is PLGA 75:25.

12. The composition of claim 5, wherein the polymer is PLGA 75:25 and is present in the formulation in an amount ranging from 5% to 30% by weight of the composition.

13. The composition of claim 5, wherein the polymer is PLGA 75:25 and is present in the formulation in an amount ranging from 10% to 20% by weight of the composition.

14. The composition of claim 5, wherein the cholesterol is present in an amount ranging from 40% to 90% by weight of the composition, the ester is present in an amount ranging from 5% to 20% by weight of the composition, the decoquinate free base is present in an amount ranging from 10% to 40% by weight of the composition, and the polylactic acid (PLA), polyglycolic acid (PGA), polycaprolactone (PCL), or poly(lactic-co-glycolic acid) is present in an amount ranging from 5% to 30% by weight of the composition.

15. A process for making the composition of claim 1, wherein the components are mixed and processed in a hot melt extruder (HME) machine with a temperature range from 70° C. to 90° C. and a screw rotation speed range from 20 rpm to 100 rpm.

16. A process according to claim 15 wherein the screw rotation speed range is from 40 rpm to 80 rpm.

17. A process according to claim 16, wherein the output products of the components from the HME machine are mechanically manipulated into a shape, a size and an amount suitable for injection by a cannula for subcutaneous or intramuscular injection.

18. A process for making the composition of claim 5, wherein the components are mixed and processed in a hot melt extruder (HME) machine with a temperature range from 70° C. to 90° C. and a screw rotation speed range from 20 rpm to 100 rpm.

19. A process according to claim 18 wherein the screw rotation speed range is from 40 rpm to 80 rpm.

20. A process according to claim 19, wherein the output products of the components from the HME machine are mechanically manipulated into a shape, a size and an amount suitable for injection by a cannula for subcutaneous or intramuscular injection.

21. A method comprising administering a therapeutically effective amount of the composition of claim 1 to a mammal to treat malaria or to provide prophylaxis against malaria.

22. A method according to claim 21, wherein the therapeutically effective amount is an amount to treat the mammal, wherein the mammal has said malaria.

\* \* \* \* \*